US 8,197,466 B2

(12) United States Patent
Yokota et al.

(10) Patent No.: US 8,197,466 B2
(45) Date of Patent: Jun. 12, 2012

(54) CONNECTOR AND INFUSION TUBE SET

(75) Inventors: Takayuki Yokota, Yamanashi-ken (JP);
Yoshinori Hishikawa, Yamanashi-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 484 days.

(21) Appl. No.: 12/447,228

(22) PCT Filed: Nov. 19, 2007

(86) PCT No.: PCT/JP2007/072345
§ 371 (c)(1),
(2), (4) Date: Apr. 27, 2009

(87) PCT Pub. No.: WO2008/062741
PCT Pub. Date: May 29, 2008

(65) Prior Publication Data
US 2010/0030195 A1 Feb. 4, 2010

(30) Foreign Application Priority Data
Nov. 24, 2006 (JP) .................. 2006-317772

(51) Int. Cl.
*A61M 25/16* (2006.01)
(52) U.S. Cl. ........................ 604/535; 604/539
(58) Field of Classification Search .......... 604/533–284, 604/96.01, 164.01, 523, 174–180
See application file for complete search history.

(56) References Cited

U.S. PATENT DOCUMENTS
2008/0103484 A1* 5/2008 Hishikawa et al. .......... 604/533

FOREIGN PATENT DOCUMENTS
| JP | 03-085791 U | 8/1991 |
| JP | 2007-121954 | 5/2007 |
| WO | WO 2006/068211 A1 | 6/2006 |

OTHER PUBLICATIONS

International Search Report for PCT/JP2007/072345, mailed Feb. 12, 2008.
Written Opinion of the International Searching Authority for PCT/JP2007/072345, mailed Feb. 12, 2008 (in Japanese).

* cited by examiner

*Primary Examiner* — Kevin C Sirmons
*Assistant Examiner* — Phillip Gray
(74) *Attorney, Agent, or Firm* — Buchanan Ingersoll & Rooney PC

(57) ABSTRACT

A connector includes a male connector section having a cavity, a female connector section having a cavity to which another male connector section the same as the male connector section can be connected, a male lock section or a female lock section, disposed adjacent to the male connector section so that the connection direction thereof is parallel to that of the male connector section, a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled, and a seal member formed from an elastic material, for maintaining liquid-tightness of the connection between the other male connector section and the female connector section in a locked condition where the other male lock section and the female lock section are coupled to each other, wherein an unlocking sound, which enables recognition of unlocking, is generated at a time of unlocking when the locked condition is released.

15 Claims, 12 Drawing Sheets

CONNECTOR AND INFUSION TUBE SET

TECHNICAL FIELD

The present invention relates to a connector and an infusion tube set.

BACKGROUND ART

In medical appliances requiring connection of passages for liquid(s) to be used for infusion, transfusion, nutrient dosing or the like, the liquid passages (circuits) must be connected and disconnected as required, when sustainedly or momentarily causing a flow of the liquid(s), such as a liquid medicine, blood, and liquid food. In such a situation, it is known to attach a connection means for connecting the liquid passages to an intermediate portion of the circuit. Typical examples of the connection means include the one described in Patent Document 1.

The connection means (connector) includes a male connector section, a female connector section, a male lock section, and a female lock section. When connection means having such a configuration are connected to each other, the male lock section on one side and the female lock section on the other side engage with each other in a locked condition, and the male connector section on one side and the female connector section on the other side communicate with each other to permit liquid to flow therethrough. When the connection means are connected to each other in the locked condition, the male lock section on one side is elastically deformed and engages with the female lock section on the other side. At the time of engagement, a locking sound (clicking), which enables confirmation (recognition) of the locked condition, is generated.

At the time of unlocking, in order to release the locked condition, however, such a sound (unlocking sound), which enables confirmation of unlocking, is not generated. Therefore, it is unknown whether unlocking has successfully been achieved or not, and there may be cases in which, for example, an operator thinks that he or she has completed the operation for unlocking the connection means once locked to each other, but where actually, unlocking has not been achieved. In such a case, the operator may think that unlocking has been achieved and may pull the connection means away from each other. In this situation, depending on the magnitude of the pulling forces, there is a risk that excessive forces might be exerted on the male lock section and the female lock section on respective sides, eventually breaking one or both of the lock sections.

Patent Document 1: International Publication No. WO 2006/068211

DISCLOSURE OF INVENTION

It is an object of the present invention to provide a connector and an infusion tube set, in which unlocking can reliably be recognized and confirmed.

In order to attain the above object, the present invention provides a connector including:

a male connector section having a cavity;

a female connector section having a cavity to which another male connector section the same as the male connector section can be connected;

a male lock section or a female lock section, disposed adjacent to the male connector section so that the connection direction thereof is parallel to that of the male connector section;

a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material, for maintaining liquid-tightness of the connection between the other male connector section and the female connector section in a locked condition where the other male lock section and the female lock section are coupled to each other, wherein an unlocking sound, which enables recognition of unlocking, is generated at a time of unlocking when the locked condition is released.

This ensures that unlocking can be recognized assuredly and reliably.

In addition, in the connector according to the present invention, preferably, in the locked condition, the cavity of the other male connector section and the cavity of the female connector section communicate with each other so as to permit liquid to flow therethrough.

This ensures that, in the locked condition, liquid can assuredly pass between the female connector section and the other male connector section.

Further, in the connector according to the present invention, preferably, the male lock section includes a pair of claw parts, which are capable of moving toward and away from each other, and an urging part provided on one end side of both the claw parts and operative to urge the claw parts so as to move the claw parts away from each other on the other end side; and the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other.

This ensures that the connector can reliably be placed in a locked condition, and that the locked condition can be released assuredly.

Further, in the connector according to the present invention, preferably, each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface;

the engaging part has an engaging part side first surface, which makes contact with the claw part side first surface in the locked condition, and an engaging part side second surface, which makes contact with the claw part side second surface in the locked condition;

wherein by operating the operating part in the locked condition, the claw part side first surface of the stepped part is caused to ride over the engaging part side first surface, thereby generating the unlocking sound.

Owing thereto, unlocking can be recognized and confirmed assuredly.

In addition, in the connector according to the present invention, preferably, the female lock section and the other male lock section are pressed in directions so as to move toward each other, at the time when the connector is placed in the locked condition.

This ensures that an operation to obtain the locked condition can be carried out easily.

Further, in the connector according to the present invention, preferably, a gap is generated between the claw part side first surface and the engaging part side first surface, immediately upon completion of the pressing operation.

This ensures that when the claw part side second surface collides against the engaging part side second surface, a comparatively strong collision occurs, so that the locked condition can be recognized (confirmed) more reliably.

Further, in the connector according to the present invention, preferably, when an imaginary plane parallel to a direction of movement of the acute angle part is assumed, the acute angle part is located so as to project from the imaginary plane.

As a result thereof, a clear unlocking sound is likely to be generated. Similarly, a clear locking sound (locking connection sound) is likely to be generated.

In addition, in the connector according to the present invention, preferably, a locking sound, which enables recognition of the locked condition, is generated when the connector is placed in the locked condition.

This makes it possible to securely recognize that the connector has been placed in the locked condition.

Further, in the connector according to the present invention, preferably, the unlocking sound and the locking sound differ from each other in tone and/or in volume.

This ensures that, by audibly perceiving the tone and/or the volume of the sound, it is possible to recognize whether the connectors have been placed in the locked condition or in the unlocked condition.

Further, in the connector according to the present invention, preferably, the seal member is affixed to the cavity of the female connector section, and includes a surface that is placed in secure contact with an end part of the other male connector section in the locked condition, and a slit formed in the surface and which is opened in the locked condition.

This ensures that, in the locked condition, the female connector section and the other male connector section are connected in a liquid-tight manner, so that liquid can pass between the connectors reliably.

In addition, preferably, the connector according to the present invention includes a plurality of female connector sections, wherein at least one of the female connector sections and the male connector section are disposed such that center lines thereof are substantially orthogonal to each other.

This makes it possible to change the direction(s) of flow of the liquid or liquids that pass through the connector.

In addition, preferably, the connector according to the present invention includes a plurality of female connector sections, wherein at least one of the female connector sections and the male connector section are disposed such that center lines thereof are parallel to each other, and such that an opening part of the female connector section and an opening part of the male connector section are oriented in opposite directions.

This ensures that, for example, when the two connectors are interconnected, the connectors can be connected to each other substantially rectilinearly, by connecting the female connector section with the other male connector section.

In order to attain the above object, the present invention further provides a connector including:

a male connector section having a cavity;

a female connector section having a cavity to which another male connector section the same as the male connector section can be connected;

a male lock section or a female lock section, disposed adjacent to the male connector section so that the connection direction thereof is parallel to that of the male connector section;

a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material for maintaining liquid-tightness of the connection between the other male connector section and the female connector section in a locked condition where the other male lock section and the female lock section are coupled to each other, wherein the male lock section includes a pair of claw parts, which are capable of moving toward and away from each other, and an urging part provided on one end side of both the claw parts and operative to urge the claw parts so as to move the claw parts away from each other on the other end side, the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other, each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface, the engaging part has an engaging part side first surface, which makes contact with the claw part side first surface in the locked condition, and an engaging part side second surface, which makes contact with the claw part side second surface in the locked condition, wherein by operating the operating part in the locked condition, the claw part side first surface of the stepped part is caused to ride over the engaging part side first surface, thereby generating the unlocking sound, and the female lock section and the other male lock section are pressed in directions so as to move toward each other, at the time when the connector is placed in the locked condition, and a gap is generated between the claw part side first surface and the engaging part side first surface, immediately upon completion of the pressing operation.

This ensures that unlocking can be recognized assuredly and reliably.

In order to attain the above object, the present invention further provides a connector including:

a male connector section having a cavity;

a female connector section having a cavity to which another male connector section the same as the male connector section can be connected;

a male lock section or a female lock section, disposed adjacent to the male connector section so that the connection direction thereof is parallel to that of the male connector section;

a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material for maintaining liquid-tightness of the connection between the other male connector section and the female connector section in a locked condition where the other male lock section and the female lock section are coupled to each other, wherein the male lock section includes a pair of claw parts, which are capable of moving toward and away from each other, and an urging part provided on one end side of both the claw parts and operative to urge the claw parts so as to move the claw parts away from each other on the other end side, the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other, each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface, the engaging part has an engaging part side first surface, which makes contact with the claw part side first surface in the locked condition, and an engaging part side second surface, which makes contact with the claw part side second surface in the locked condition, wherein by operating the operating part in the locked condition, the claw part side first surface of the stepped part is caused to ride over the engaging part side first surface, thereby generating the unlocking sound, and when an imaginary plane parallel to a direction of movement of the acute angle part is assumed, the acute angle part is located so as to project from the imaginary plane.

This ensures that unlocking can be recognized assuredly and reliably.

In order to attain the above object, the present invention also provides an infusion tube set including:

the connector according to the present invention; and a tube assembly having a tube, and a tube-side connector, which is disposed at one end portion of the tube, and which can be connected to the connector.

This makes it possible to reliably recognize that unlocking has occurred.

BEST MODE FOR CARRYING OUT THE INVENTION

The connector and the infusion tube set according to the present invention will be described in detail below, based on a preferred embodiment thereof as shown in the accompanying drawings.

Figure 1:
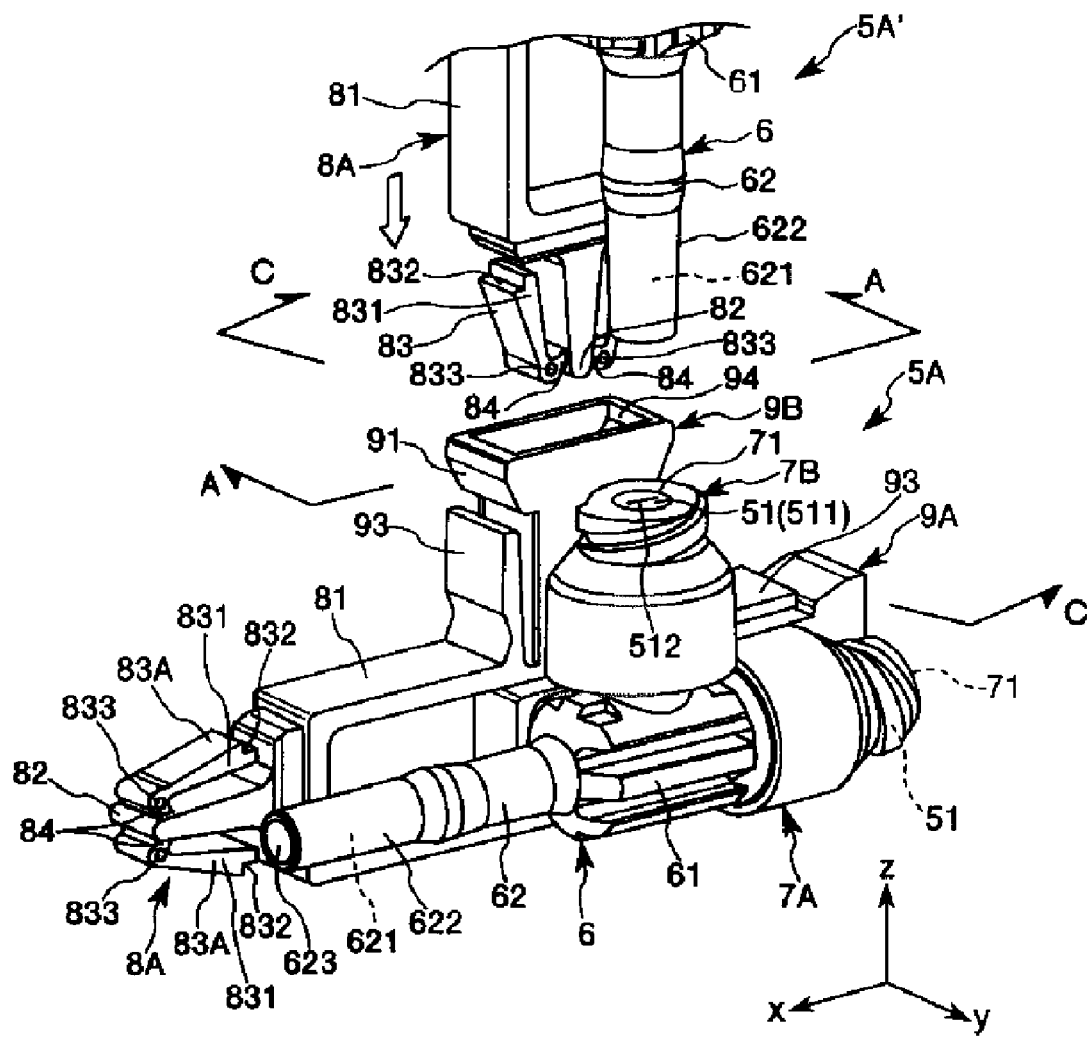
FIG. 1 is a perspective view showing a connector according to the present invention.
Figure 2:
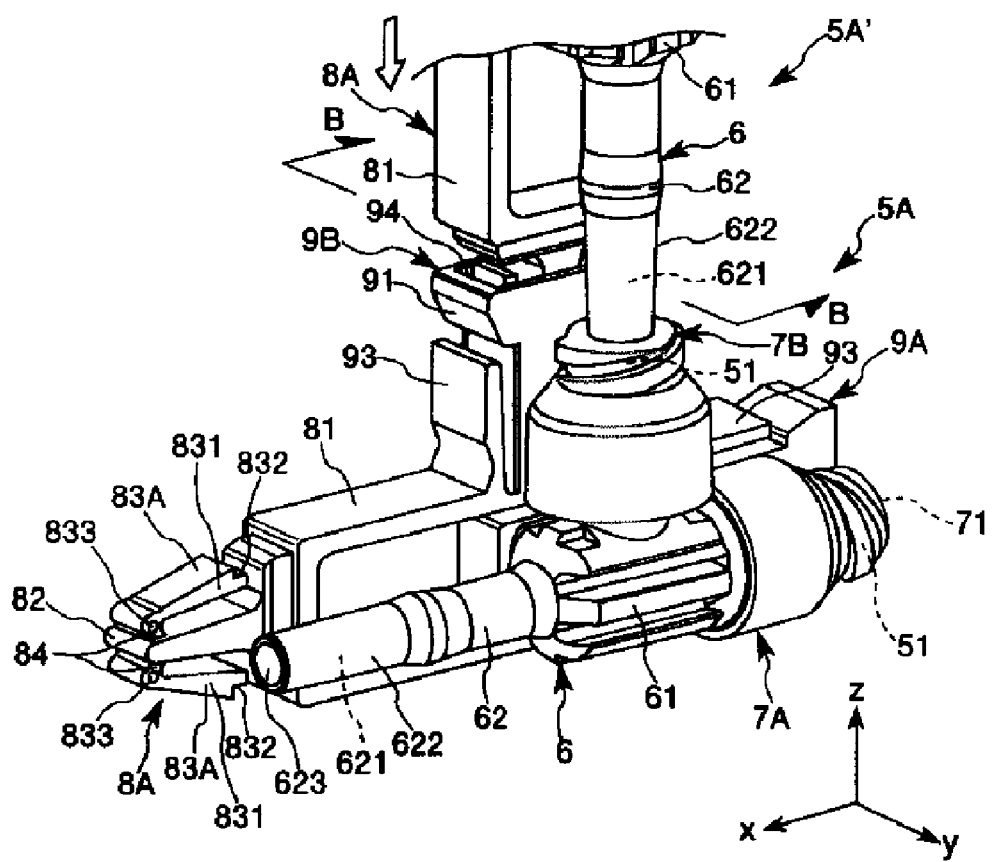
FIG. 2 is a perspective view showing the connector according to the present invention.
Figure 3:
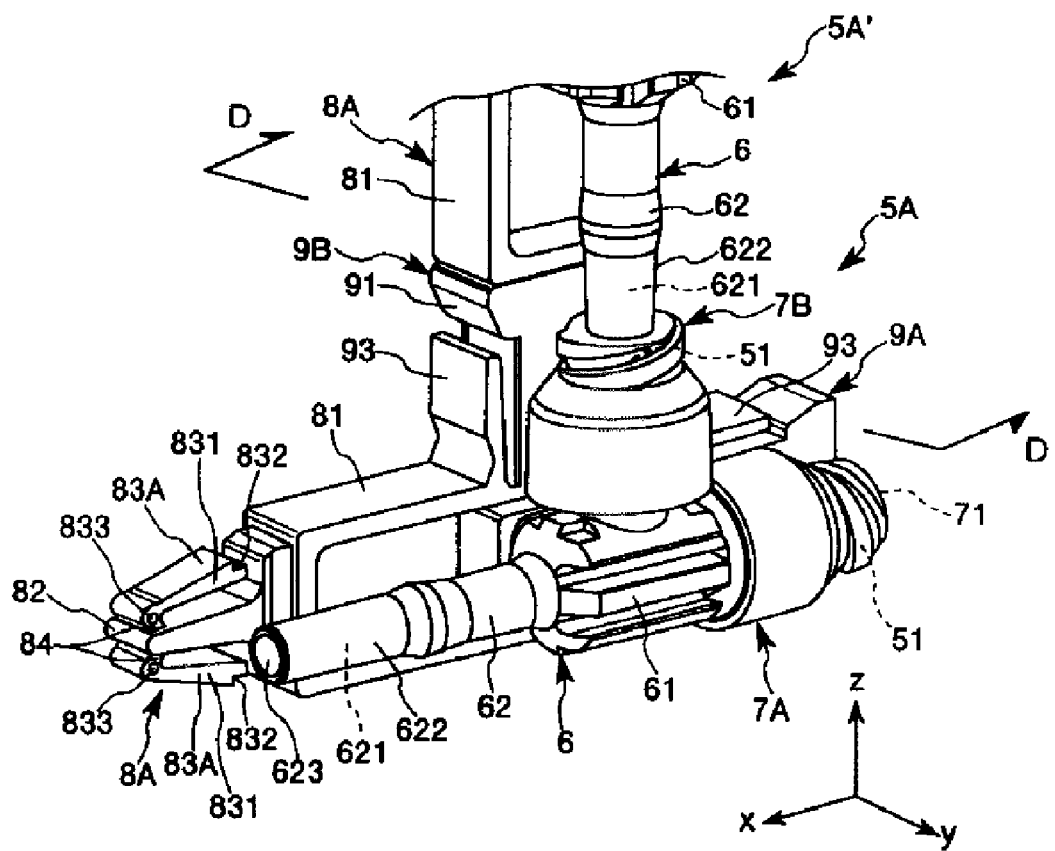
FIG. 3 is a perspective view showing the connector according to the present invention.
Figure 4:
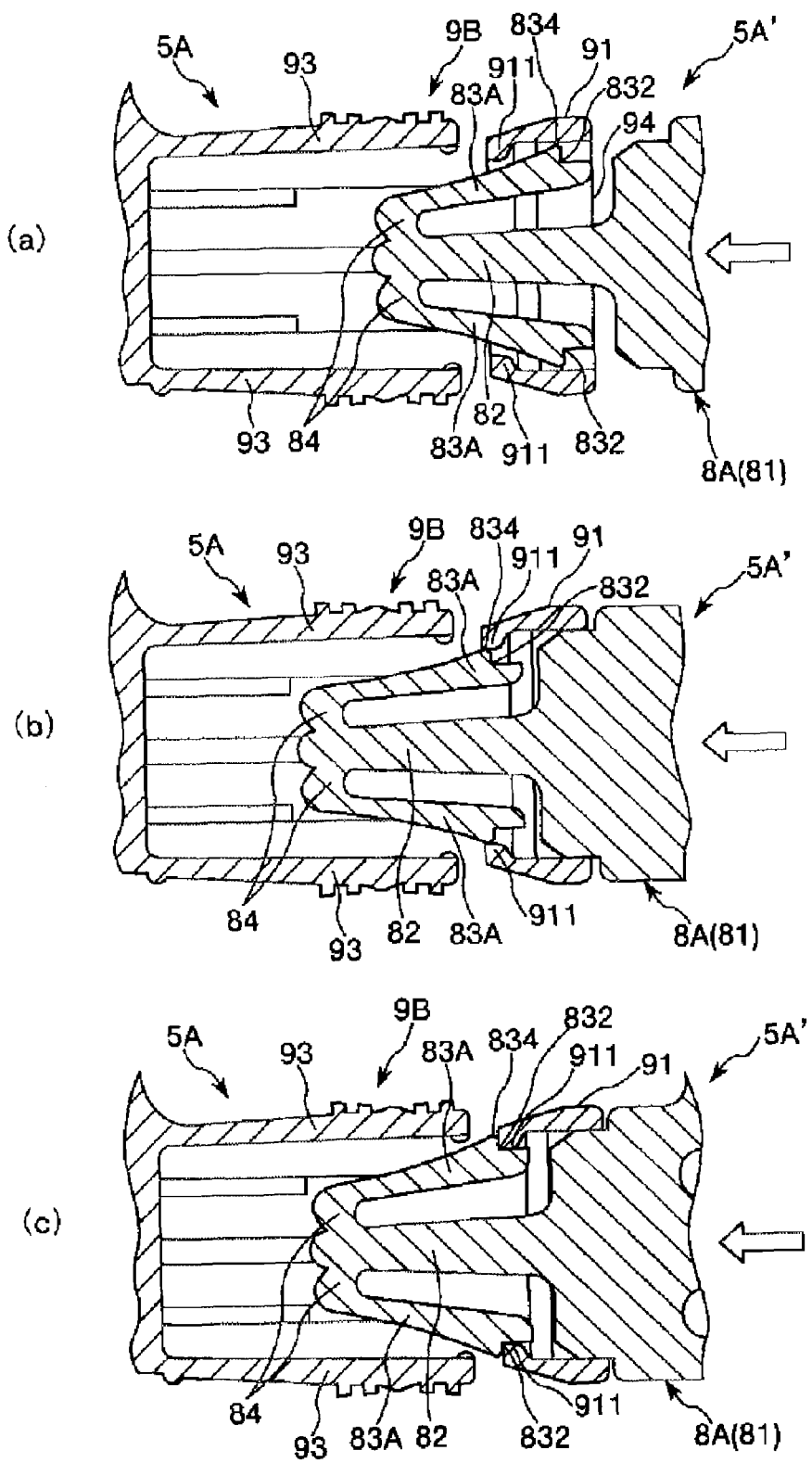
FIG. 4 illustrates sectional views taken along line A-A of FIG. 1.
Figure 5:
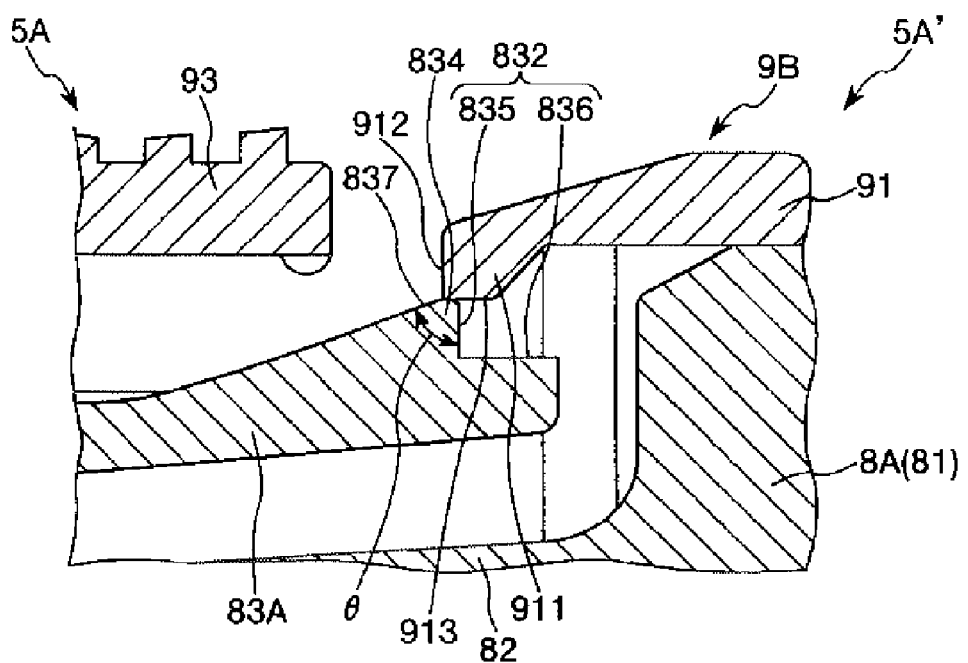
FIG. 5 is a partially enlarged detailed view of FIG. 4(*b*)
Figure 6:
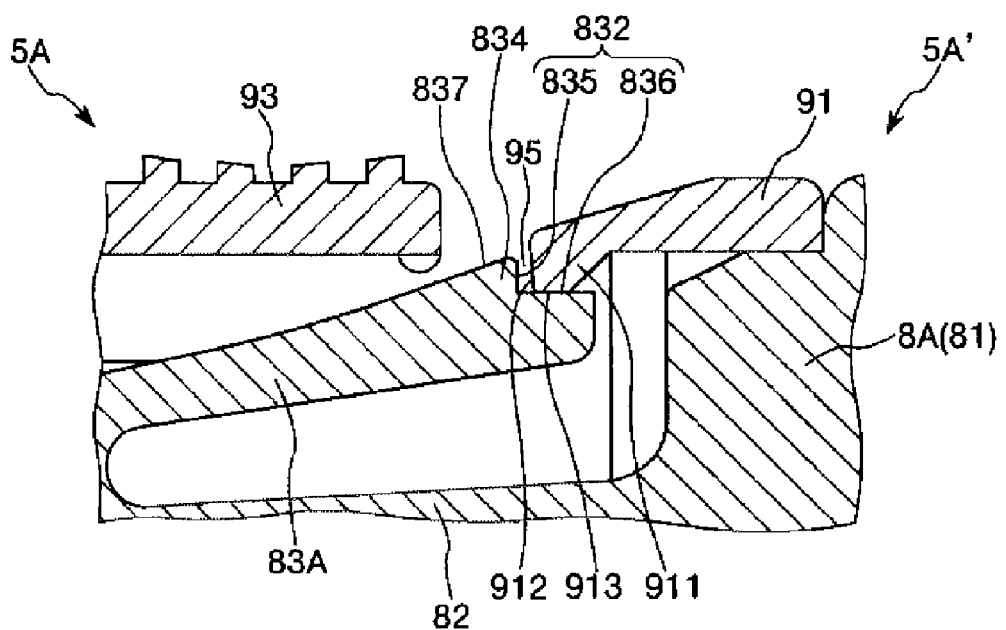
FIG. 6 is a partially enlarged detailed view of FIG. 4(*c*)
Figure 7:
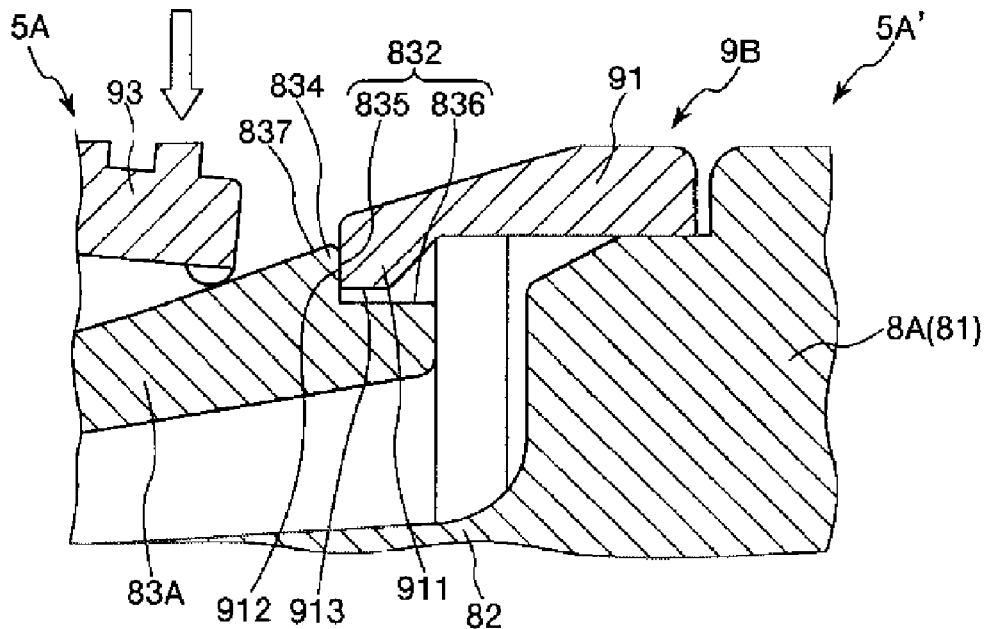
FIG. 7 is a partially enlarged detailed view (sectional view) sequentially illustrating an unlocked condition of the connector shown in FIG. 1.
Figure 8:
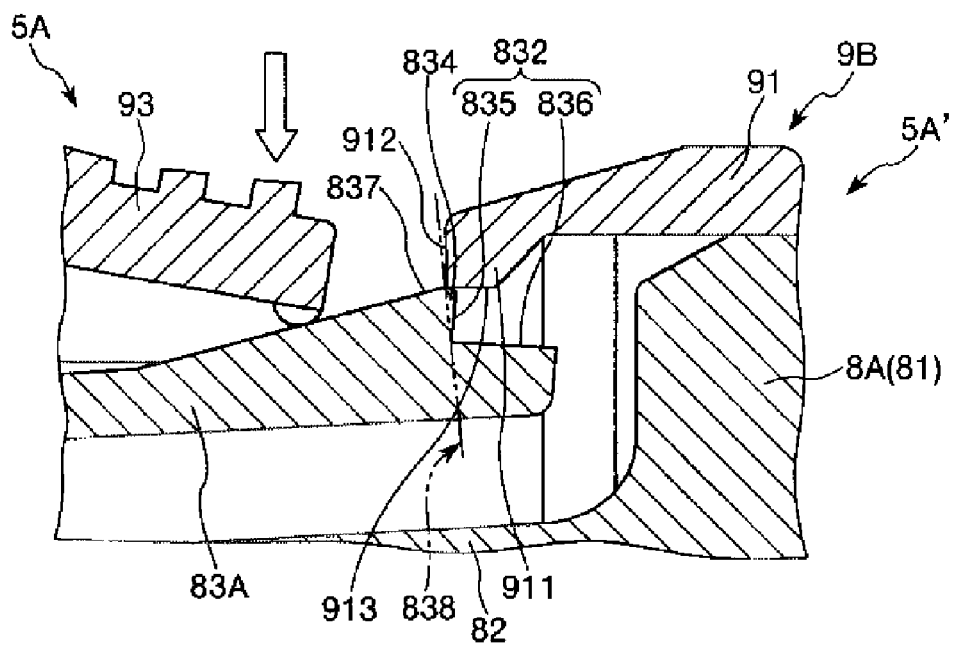
FIG. 8 is a partially enlarged detailed view (sectional view) sequentially illustrating the unlocked condition of the connector shown in FIG. 1.
Figure 9:
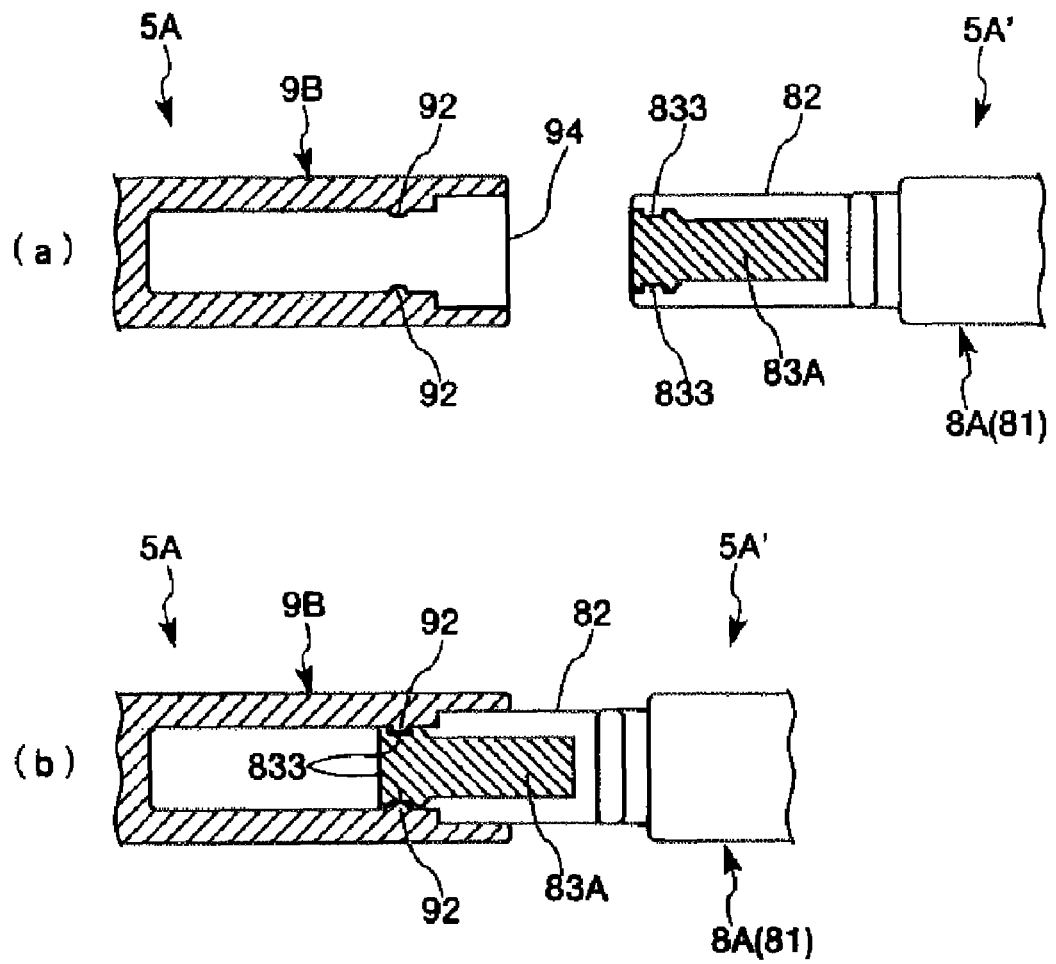
FIG. 9 illustrates sectional views taken along line B-B of FIG. 2.
Figure 10:
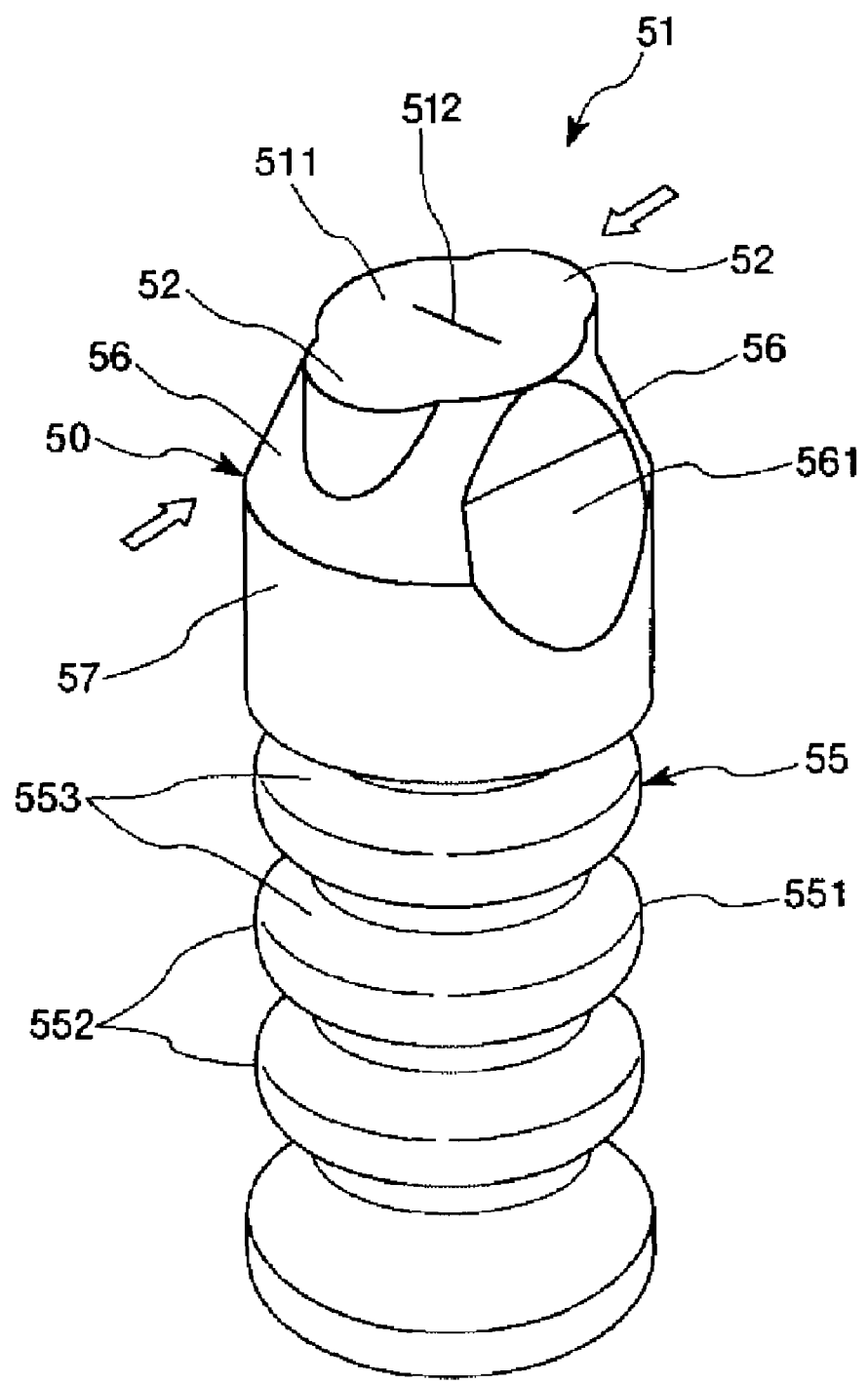
FIG. 10 is a perspective view showing a valve element (seal member) possessed by the connector shown in FIG. 1.
Figure 11:
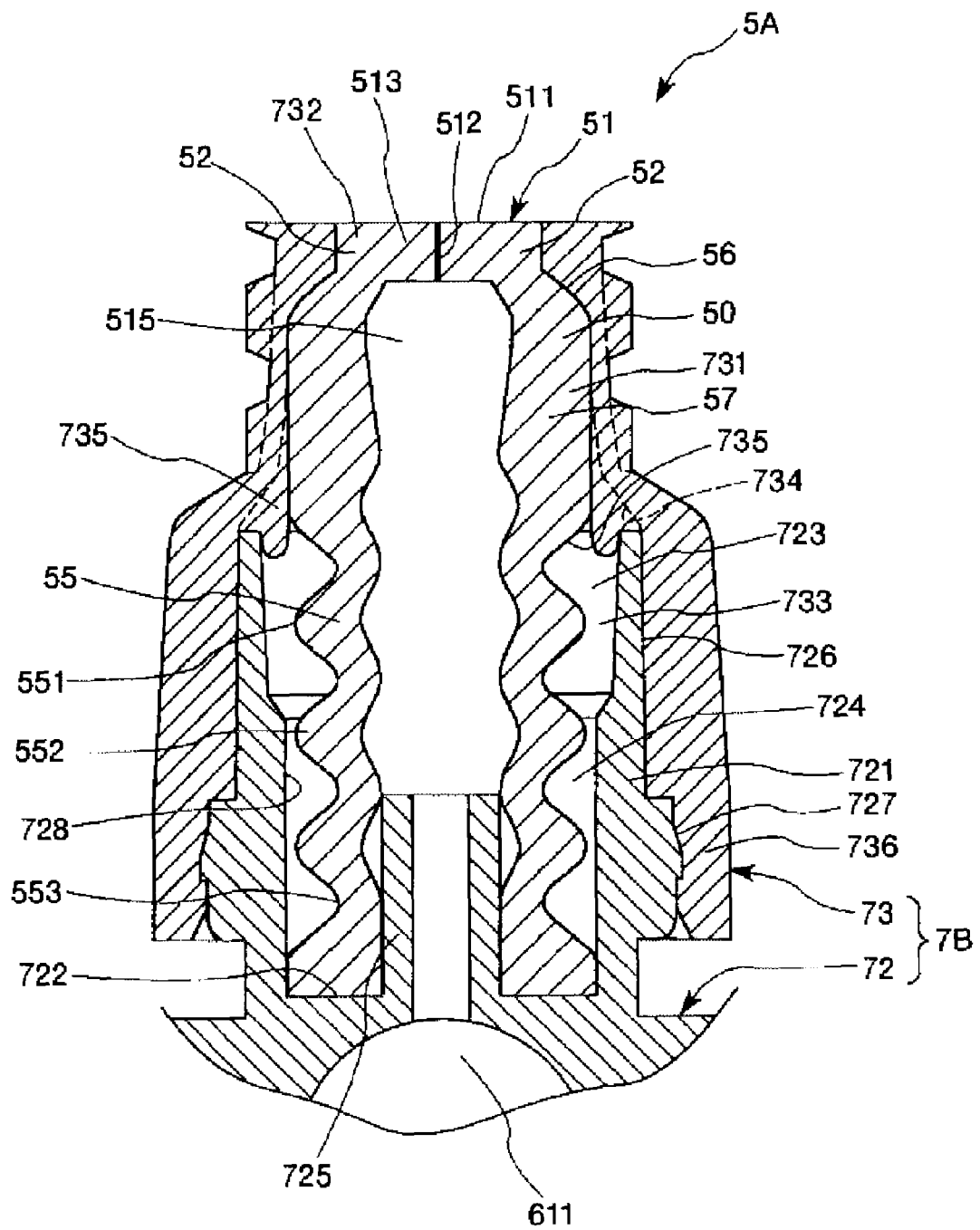
FIG. 11 is a sectional view taken along line C-C of FIG. 1.
Figure 12:
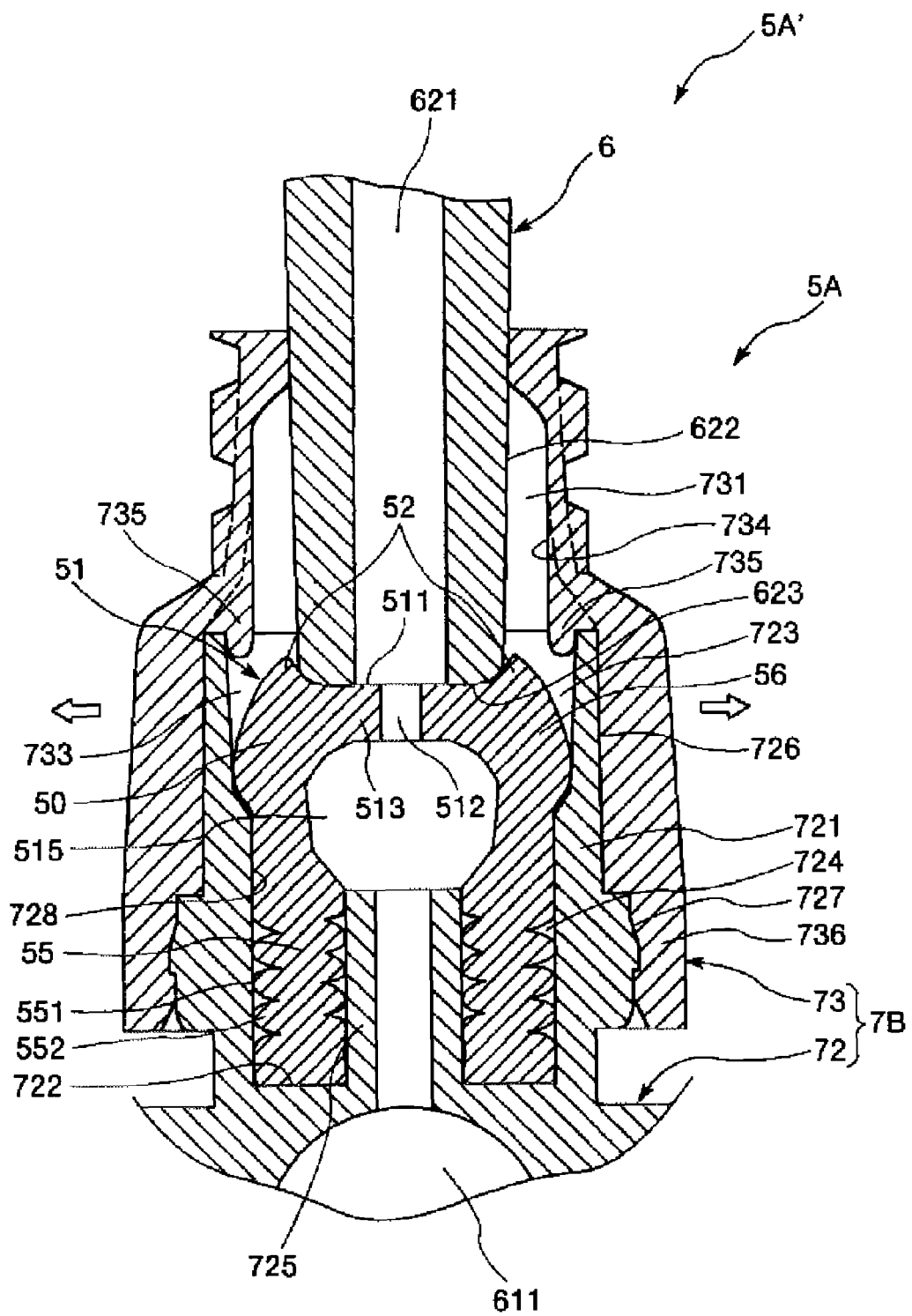
FIG. 12 is a sectional view taken along line D-D of FIG. 3.
Figure 13:
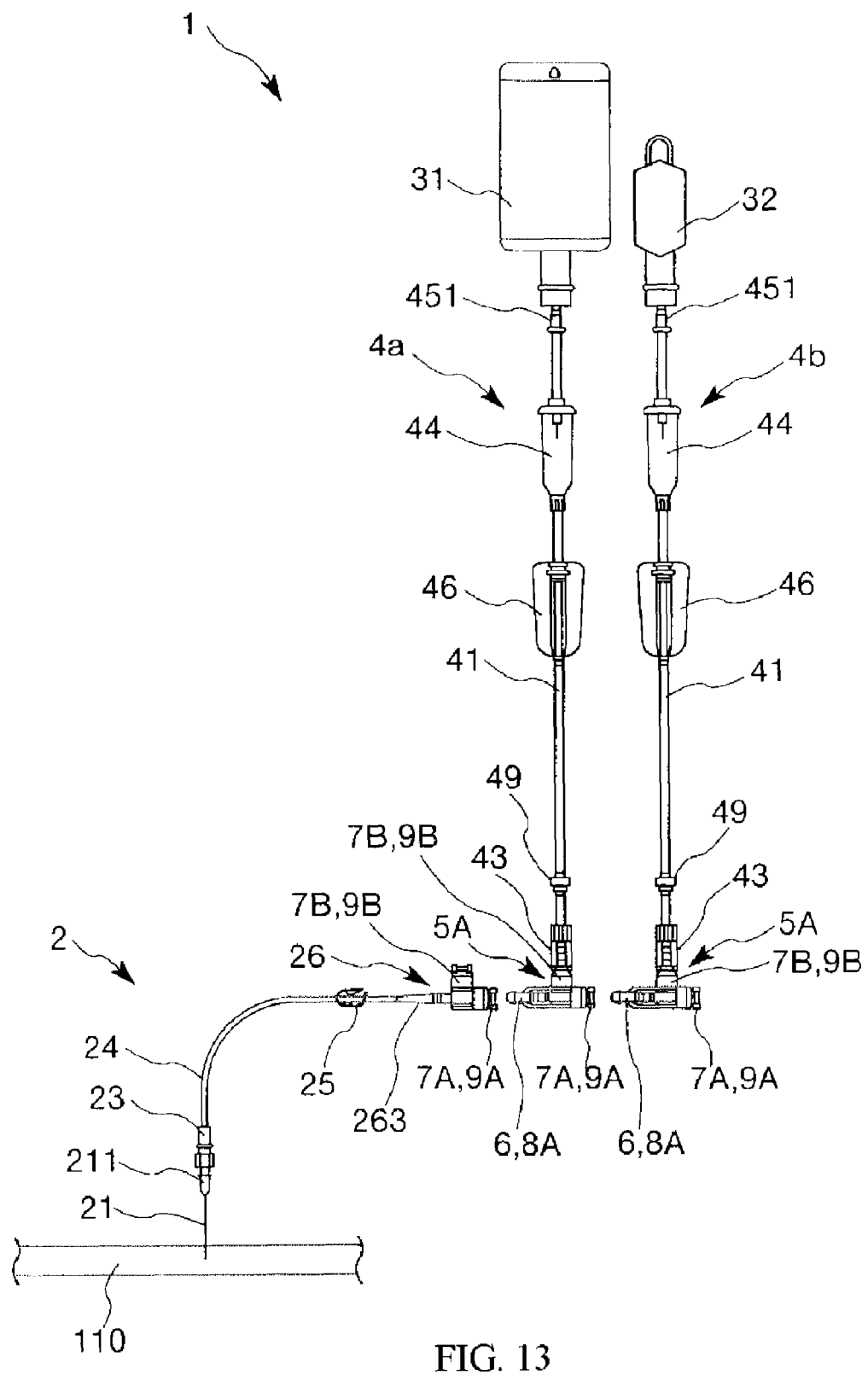
FIG. 13 is a plan view of an infusion tube set according to the present invention, which incorporates the connector shown in FIG. 1.
Figure 14:
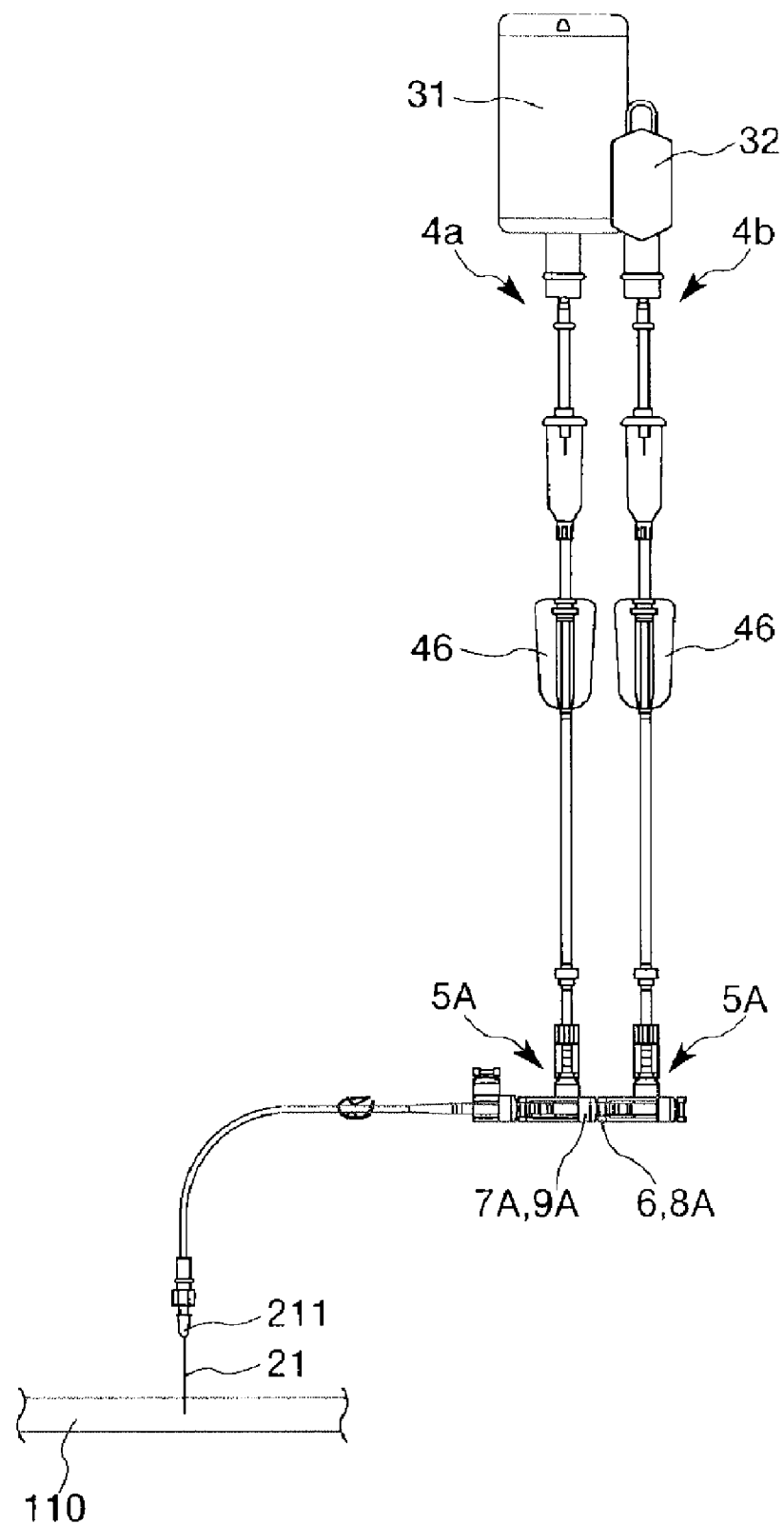
FIG. 14 is a plan view of the infusion tube set shown in FIG. 13, showing a condition in which respective infusion tubes are connected thereto.

FIGS. 1 to 3 are perspective views respectively showing the connector according to the present invention; FIG. 4 illustrates sectional views taken along line A-A of FIG. 1; FIG. 5 is a partially enlarged detailed view of FIG. 4(*b*); FIG. 6 is a partially enlarged detailed view of FIG. 4(*c*); FIGS. 7 and 8 are partially enlarged detailed views (sectional views) sequentially illustrating an unlocked condition of the connector shown in FIG. 1; FIG. 9 illustrates sectional views taken along line B-B of FIG. 2; FIG. 10 is a perspective view showing a valve element (seal member) possessed by the connector shown in FIG. 1; FIG. 11 is a sectional view taken along line C-C of FIG. 1; FIG. 12 is a sectional view taken along line D-D of FIG. 3; FIG. 13 is a plan view of an infusion tube set according to the present invention, which incorporates the connector shown in FIG. 1; and FIG. 14 is a plan view of the infusion tube set shown in FIG. 13, showing a condition in which respective infusion tubes are connected thereto. Incidentally, for facilitating descriptions thereof, the longitudinal direction of the connector will be referred to as an "x-axis direction," and directions perpendicular to the x-axis direction will be referred to as a "y-axis direction" and a "z-axis direction" respectively. Further, in the following descriptions, in FIGS. 10 to 14, the lower side will be referred to as a "distal" side and the upper side as a "proximal" side.

The infusion tube set (infusion set) 1 shown in FIGS. 13 and 14 is an apparatus (set) utilized for injecting (administering) an infusion into a living organism (patient).

The term infusion includes all liquids that can be administered to living organisms, for example, liquid medicines, correcting electrolytes, and physiological saline.

In addition, the drug in the liquid medicine is not particularly limited, and may be any drug, such as a sedative, intravenous anesthetic, anesthetic analgesic, local anesthetic, antidepolarizing muscle relaxant, vasopressor, depressor, coronary vasodilator, diuretic, antiarrhythmic agent, bronchodilator, styptic, vitamin agents, antibiotic agents, and a lipid emulsion.

As shown in FIG. 13, the infusion tube set 1 includes a first infusion tube (first tube assembly) 4b, a second infusion tube (second tube assembly) 4a, connectors 5A to which one-side end parts of the first infusion tube 4b and the second infusion tube 4a can be connected, piercing needles (hollow needles or spikes) 451 (connecting parts) provided respectively at other end parts of the first infusion tube 4b and the second infusion tube 4a, and an infusion dosing section 2 for dosing a patient with an infusion or infusions. These components will be described sequentially below.

The connector 5A on the first infusion tube 4b side (the right side in FIG. 13) and the connector 5A on the second infusion tube 4a side (the left side in FIG. 13) are substantially the same in configuration. Taking this into account, therefore, the connector 5A on the second infusion tube 4a side will be described below as representative.

As shown in FIGS. 1 to 3, the connector 5A includes a male connector section 6, female connector sections 7A and 7B, a male lock section 8A, female lock sections 9A and 9B, and a valve element (seal member) 51. Incidentally, FIGS. 1 to 3 show the connector 5A and the connector 5A' in a condition prior to connection thereof, the connector 5A and the connector 5A' in a half-locked condition, and the connector 5A and the connector 5A' in a locked condition, respectively.

Here, the term "connector 5A'" implies a connector having a male connector section 6 and a male lock section 8A, which are the same as those of the connector 5A. The connector corresponds to a connector (tube-side connector) 43 that is possessed by the second infusion tube 4a, which will be described later.

Herein, the term "half-locked condition" implies a condition in which the connector 5A and the connector 5A' are not fully connected with each other, and more specifically, a condition in which the connector 5A and the connector 5A' can easily be moved away from each other.

Further, the term "locked condition" implies a the condition in which the connector 5A (the female lock section 9B) and the connector 5A' (the male lock section 8A) are fully connected with each other, and more specifically, a condition in which the connection between the connector 5A and the connector 5A' is not released, unless operating parts 93 of the female lock section 9B of the connector 5A, to be described later, are operated.

As shown in FIG. 1 (and also in FIGS. 2 and 3), the male connector section 6 has a male connector section main body 61, and a tubular section 62.

The tubular section 62 is formed to project in the x-axis positive direction from the male connector section main body 61. The tubular section 62 has a liquid passage (cavity) 621 through which liquid passes, and a luer tapered part 622.

The liquid passage 621 communicates with the interior of the male connector section main body 61.

The luer tapered part 622 is formed on an outer peripheral part of the male connector section 6, which is on the side of an opening part 623, in such a manner that the outside diameter thereof gradually decreases toward the opening part 623.

Each of the female connector sections 7A and 7B forms a portion to which the male connector section 6 of the connector 5A' can be connected, respectively. The female connector section 7A and the female connector section 7B are substantially the same in shape (configuration); taking this into consideration, the female connector section 7B will be described below as representative.

As shown in FIG. 11, the female connector section 7B has a female connector section main body 72, and a cap section (cap) 73.

The female connector section main body 72 shown in FIG. 11 is formed, at a distal portion thereof, with a valve element disposing section 721 having a bottomed cylindrical shape. The valve element disposing section 721 is formed with a second cavity (cavity) 723 therein on the proximal side, and with a third cavity (cavity) 724 on the distal side thereof, which communicates with the second cavity 723. The second cavity 723 has a larger inside diameter than a first cavity (cavity) 731 formed in the cap section 73, to be described later. The third cavity 724 (inner peripheral surface 728) has a smaller inside diameter than the second cavity 723. The inside diameter of the third cavity 724, preferably, is slightly larger than the outside diameter of a barrel part 55 (an outer peripheral surface 551) of the valve element 51, to be described later.

In addition, at a central portion of a bottom surface 722 of the female connector section main body 72, an internal projection 725 is provided, which is constituted by a tubular body. When the male connector section 6 is connected to the first cavity 731 (connection port 732) and the valve element 51 begins to be pressed, the inside portion of the valve element 51 is supported by the internal projection 725, so that buckling of the valve element 51 (bending of the valve element 51 into a V-shape) can be prevented from occurring (see FIG. 12). Further, when a liquid passes through the connector 5A, stagnation of the liquid can be prevented.

In addition, a lumen of the internal projection 725 communicates with a passage 611, which is formed inside the male connector section main body 61, and through which liquid can pass. This ensures that the second cavity 723 and the third cavity 724 communicate with the passage 611 through the internal projection 725.

Also, on the distal side of the outer peripheral surface 726 of the valve element disposing section 721, a stepped part 727, which is set larger in diameter than the portion on the proximal side thereof, is provided.

The cap section 73 shown in FIG. 11 is provided with a space (cavity) therein containing the valve element 51. The cap section 73 is coupled to the proximal side (the valve element disposing section 721) of the female connector section main body 72.

The cap section 73 is provided with the first cavity 731 therein, in which a head part 50 of the valve element 51, to be described later, can be inserted. The cap section 73 further includes a fitting part 733, which communicates with the first cavity 731, and which is larger in diameter than the first cavity 731.

The first cavity 731 is formed in a shape corresponding to an outer shape of the head part 50 of the valve element 51. In addition, the connection port (connecting part) 732 that connects to the male connector section 6 is formed on the proximal side of the first cavity 731, and the diameter thereof is set smaller than the diameter of the first cavity 731 on the distal side.

The first cavity 731 is provided at its inner peripheral surface 734 with a plurality of ribs 735, which extend along the axial direction and project in a radial direction of the first cavity 731. When the male connector section 6 is connected to the connector 5A (the connection port 732), the valve element 51 is supported by the ribs 735, whereby buckling of the valve element 51 (and falling off of the valve element 51) can be prevented from occurring. In addition, the number of ribs 735 is not particularly limited; for example, the number is preferably two to ten, and more preferably, four to eight.

A stepped part 736, in which the stepped part 727 of the valve element disposing section 721 is to be fitted, is formed on the distal side of the fitting part 733, and the diameter thereof is set to be larger than the diameter of the fitting part 733 on the proximal side. In addition, the inside diameter of the stepped part 736, preferably, is approximately equal to or slightly smaller than the outside diameter of the stepped part 727 of the valve element disposing section 721. This enables firm fitting (coupling) (liquid-tight contact) between the cap section 73 (the stepped part 736) and the female connector section main body 72 (the stepped part 727), and thus liquid inside the connector 5A can be prevented from leaking. Further, when the cap section 73 and the female connector section main body 72 are coupled together, the first cavity 731 and the second cavity 723 communicate with each other, and the valve element 51 can be disposed (contained) within the space composed of the first cavity 731, the second cavity 723, and the third cavity 724.

Incidentally, the method for fixing the female connector section main body 72 and the cap section 73 to each other is not limited to the aforementioned fitting. For example, the method may be performed by caulking, adhesion with an adhesive, fusing such as heat fusing and ultrasonic fusing, or the like.

As shown in FIG. 1 (also in FIGS. 2 and 3), the female connector section 7A is disposed in an x-axis negative direction in relation to the male connector section main body 61 (the male connector section 6). In other words, the female connector section 7A is disposed such that the center line thereof is parallel to the center line of the male connector section 6, and so that the opening part 71 of the female connector section 7A and an opening part 623 of the male connector section 6 are oriented in opposite directions.

This ensures that when the two connectors 5 are connected to each other, for example, the connectors 5 can be connected substantially rectilinearly, by connecting the male connector section 6 on one side and the female connector section 7A on the other side.

The female connector section 7B is disposed in a z-axis positive direction in relation to the male connector section main body 61 (the male connector section 6). In other words, the female connector section 7B is disposed such that the center line thereof is substantially orthogonal to the center line of the male connector section 6.

When such female connector sections 7A and 7B are provided, liquids can be fed into the male connector section 6 from two different directions, and the liquids can branch off from the male connector section 6 in two different directions.

As shown in FIGS. 11 and 12, the valve elements 51 are contained (fixed), respectively, in the female connector section 7A and the female connector section 7B.

The valve elements 51 are each formed from an elastic material. Examples of suitable elastic materials include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., and various thermoplastic elastomers based on styrene, polyolefin, polyvinyl chloride, polyurethane, polyester, polyamide, polybutadiene, trans-polyisoprene, fluororubber, chlorinated polyethylene, or the like, which may be used either singly or in a mixture of two or more of them. When such an elastic material is used, an appropriate elasticity can be imparted to a top face 511 of the valve element 51, and therefore, the top face 511 can be placed in secure contact with the opening part (end part) 623 of the male connector section 6 (see FIG. 12).

As shown in FIG. 10, the valve element 51 includes the head part 50, and the barrel part 55, which is provided (formed) on the distal side of the head part 50.

The head part 50 has a bottomed cylindrical shape, and is formed with a cavity 515 therein through which liquid can pass, together with a slit 512 that extends from the flat top face 511 (a bottom part 513) to reach the cavity 515. The slit 512 is formed substantially in the shape of a straight line segment. The simple shape of the slit 512 enables easier (more assured) opening of the slit 512. In addition, the flat shape of the top face 511 permits the top face 511 (the slit 512) to be disinfected easily.

As shown in FIG. 1, the top face 511 is exposed from the opening part 71 of the female connector section 7A. Further, the top face 511 is located substantially flush with an end face of the female connector section 7A.

The head part 50 includes a tapered part 56 having an outside diameter in the vicinity of the top face 511 that gradually increases (in the axial direction) toward the barrel part 55, and a constant outside diameter part 57 provided at the distal end of the tapered part 56.

In addition, the tapered part 56 is formed with cutout portions 561 therein where the tapered part 56 is partially removed. Specifically, the head part 50 is formed with such cutout portions 561, where material is removed in areas ranging from the tapered part 56 to the constant outside diameter part 57.

This ensures that when the male connector section 6 of the connector 5A', which is connected to (inserted into) the connector 5A, is pulled off, i.e., when the locked condition is released, the valve element 51 (the head part 50) can enter easily into the first cavity 731 of the cap section 73, and therefore, the slit 512 can be closed more reliably.

In addition, the head part 50 is provided with two protuberant contact portions 52, which are pressed at times when the slit 512 is closed. The two contact portions 52 are formed in the vicinity of the top face 511 of the head part 50, and project in directions opposite to the directions (the directions of arrows in FIG. 10) in which the slit 512 is closed.

The presence of the contact portions 52 ensures that when the head part 50 is inserted into the first cavity 731 of the cap section 73, the inner peripheral surface 734 of the first cavity 731 presses against the contact portions 52, so that the slit 512 can be closed more reliably (see FIG. 11). In addition, this makes it possible to enhance pressure resistance against the pressure of the liquid inside the connector 5A (internal pressure).

When the male connector section 6 of the connector 5A' is not connected, the head part 50, configured as described above, is inserted into the first cavity 731 of the cap section 73, with the slit 512 being closed (see FIG. 11).

As shown in FIG. 10, the barrel part 55 includes a bellows-like cylindrical body. Specifically, the barrel part 55 has a bellows-like overall shape, in which large diameter ring portions 552 and small diameter ring portions 553 are alternately arrayed along the axial direction. Such a barrel part 55 functions as a deforming section (urging means), for urging the valve element 51 from the distal side toward the proximal side (i.e., in the direction in which the head part 50 is inserted into the first cavity 731 of the cap section 73).

Since the barrel part 55 functions as a deforming section, it is unnecessary to separately provide a component part on the connector 5A serving as an urging means. Therefore, a reduction in the number of component parts, and simplification in structure, can be realized.

In addition, although the barrel part 55 provides most of the restoring force for restoring the valve element 51 from the distal side toward the proximal side, the head part 50 may also provide a portion of the restoring force.

As shown in FIG. 1, the male lock section 8A of the connector 5A (the connector 5A' also) has a base part (male lock section main body) 81, a projected part 82 that projects from the base part 81, a pair of claw parts 83A, 83A provided on the projected part 82, and urging parts 84, which act to urge each of the claw parts 83A, respectively.

The base part 81 has an elongate shape.

In the y-axis positive direction relative to the base part 81 (the male lock section 8A), the male connector section main body 61 of the male connector section 6 is secured (affixed) adjacent to the base part 81. Further, in the x-axis positive direction relative to the base part 81, a projected part 82 is formed that projects in the x-axis positive direction.

In z-axis directions (the upward and downward directions in FIG. 1) relative to the projected part 82, the claw parts 83A and 83A are provided respectively. Specifically, the claw parts 83A and 83A are disposed oppositely to each other, with the projected part 82 residing therebetween. Both of the claw parts 83A, 83A have a long (platelet-like) shape, and end portions (other end portions) 831 thereof move toward and away from each other along the z-axis direction.

As shown in FIGS. 4 to 8, each of the claw parts 83A has a stepped part (first male-side engaging part) 832 and an acute angle part 834, which are provided at the end portion 831 thereof (see also FIGS. 1 and 2).

As shown in FIG. 5 (also in FIGS. 6 to 8), the stepped part 832 forms a portion where the thickness of the end portion 831 of the claw part 83A varies sharply. The stepped part 832 has two flat surfaces, which are L-shaped in side view (as viewed in the y-axis direction). In other words, the stepped part 832 has a claw part side first surface 835, which is substantially parallel to the z-axis direction (the direction in which the claw parts 83A move toward and away from each other), and a claw part side second surface 836, which is substantially perpendicular to the claw part side first surface 835.

The acute angle part 834 has a claw part side third surface 837, which is adjacent to the claw part side first surface 835. The claw part side third surface 837 is an inclined surface, which forms an acute angle with the claw part side first surface 835.

In addition, each claw part 83A is provided with recesses (second male-side engaging parts) 833, respectively, on both side surfaces of an end portion (one end portion) thereof.

In the vicinity of each recess 833, urging parts 84 are provided, respectively, for coupling the projected part 82 and each claw part 83A to each other. Each urging part 84 urges each of the claw parts 83A, so that the end portions 831 (the stepped parts 832) of both of the claw parts 83A, 83A move away from each other.

The male lock section 8A thus configured is located at a position corresponding to (adjacent to) the male connector section 6 (see FIG. 1). In addition, the male lock section 8A and the male connector section 6 are formed respectively along the x-axis direction, i.e., the connection directions (projection directions) thereof are parallel to each other.

As shown in FIG. 1, the female lock sections 9A and 9B make up portions to which the male lock section 8A of the connector 5A' can be coupled, respectively.

The female lock section 9A is disposed in the x-axis negative direction in relation to the base part 81 (the male lock section 8A). In addition, the female lock section 9B is disposed in the z-axis positive direction in relation to the base part 81 (the male lock section 8A). The female lock section 9A and the female lock section 9B are substantially the same in shape (configuration). Taking this into account, therefore, only the female lock section 9B will be described below as representative.

The female lock section 9B has a substantially tubular overall shape.

As shown in FIGS. 4 and 9, the female lock section 9B is provided with a first female-side engaging part (engaging part) 91, which is capable of engagement with each of the stepped parts 832 (each claw part 83A) of the male lock section 8A of the connector 5A', second female-side engaging parts 92, which are capable of engagement with each of the recesses 833 of the male lock section 8A of the connector 5A', and operating parts (operating pieces) 93 that are capable of operating each of the claw parts 83A of the male lock section 8A of the connector 5A'.

As shown in FIG. 4, the first female-side engaging part 91 includes projected parts 911, where intermediate portions of the inner peripheral part of the female lock section 9B project inwardly. The projected part 911 has an engaging part side first surface 912, which makes contact with (corresponds to) the claw part side first surface 835 in the locked condition, and an engaging part side second surface 913, which makes contact with the claw part side second surface 836 in the locked condition (see FIGS. 4(c), 6 and 7).

As shown in FIG. 9(a), the second female-side engaging parts 92 are each provided so as to project at intermediate portions of the inner peripheral surface of the female lock section 9B, at positions different from those of the projected parts 911. When the second female-side engaging parts 92 engage within the recesses 833 in the male lock section 8A of the connector 5A', as shown in FIG. 9(b), the connector 5A and the connector 5A' are placed in a half-locked condition.

As shown in FIG. 1, the operating part 93 is composed of a small piece provided in the z-axis direction in relation to the first female-side engaging part 91. The operating part 93 operates (presses) each claw part 83A so that the end portions 831 of both the claw parts 83A of the connector 5A' (the male lock section 8A) in the locked condition come toward each other.

In addition, the operating part 93 is formed such that the outer surface thereof is substantially flush with the outer surface of the first female-side engaging part 91. This ensures that unintentional touching (pressing) of the operating part 93 can be prevented. In other words, unintentional release of the locked condition can be prevented from occurring.

The female lock section 9B thus configured is located at a position corresponding to (adjacent to) the female connector section 7B (see FIG. 1). Further, the female lock section 9B and the female connector section 7B are each formed along the z-axis direction. In other words, connection directions (formation directions) thereof are parallel to each other.

Thus, in the connector 5A, the male components (the male lock section 8A and the male connector section 6) correspond to each other, whereas the female components (the female lock section 9B and the female connector section 7B) correspond to each other. This ensures that the connector 5A and the connector 5A' can be connected accurately (assuredly) by confirming the female connector section 7B and the male connector section 6, as well as by confirming the female lock section 9B and the male lock section 8A.

Incidentally, a configuration may be adopted in which the female lock section 9B and the male connector section 6 are located adjacent to each other, whereas the male lock section 8A and the female connector section 7B are located adjacent to each other.

Incidentally, the number of the recesses 833 formed is not limited to four, and may be another even number, such as two or six.

Next, a process of connecting (in a half-locked condition, and a locked condition) and further of unlocking the connector 5A and the connector 5A' (establishing an unlocked condition, where the locked condition is released) will be described below. Incidentally, while the connector 5A' has two respective claw parts 83A, the connection processes of the claw parts 83A are equivalent, and therefore, only the claw part 83A on one side (the upper side in FIG. 4) will be described.

As shown in FIG. 1 (also FIG. 9(*a*)), starting from the condition where the connector 5A and the connector 5A' are separated from each other, the male lock section 8A of the connector 5A' is brought closer in proximity to the female lock section 9B of the connector 5A.

As shown in FIG. 4(*a*), the male lock section 8A of the connector 5A' is inserted into the female lock section 9B of the connector 5A through the opening part 94 of the female lock section 9B.

When the male lock section 8A of the connector 5A' is pressed further into the female lock section 9B of the connector 5A, as shown in FIGS. 4(*b*) and 5, the engaging part side second surface 913 of the first female-side engaging part 91 (the projected part 911) of the connector 5A presses against the claw part side third surface 837 (the top part of the acute angle part 834) of the claw part 83A of the connector 5A'.

In this instance, as shown in FIG. 9(*b*), the recesses 833 of the connector 5A' engage with the second female-side engaging parts 92 of the connector 5A. More specifically, the connector 5A' and the connector 5A are placed in a half-locked condition. In this instance, the male lock section 8A (the opening part 623) of the connector 5A' and the female lock section 9B (the top face 511) of the connector 5A are in contact with (in proximity to) each other. This ensures that, when shifting from the half-locked condition into the locked condition, the end face of the male connector section 6 of the connector 5A' can quickly press against the top face 511 of the valve element 51 of the connector 5A.

When the male lock section 8A of the connector 5A' is further pressed into the female lock section 9B of the connector 5A, the engagement between the recesses 833 of the connector 5A' and the second female-side engaging parts 92 is released, i.e., the half-locked condition is released.

When the male lock section 8A of the connector 5A' and the female lock section 9B of the connector 5A are brought further toward each other (i.e., pressed in such directions so as to approach each other) from this condition, a fully locked condition is obtained. In other words, the claw part side third surface 837 of the claw part 83A of the connector 5A' reaches beyond the engaging part side second surface 913 of the first female-side engaging part 91 of the connector 5A. Thereafter, the claw part 83A of the connector 5A' is flipped to the outside (the upper side in FIG. 6) by the urging part 84.

The engaging part side second surface 913 of the first female-side engaging part 91 of the connector 5A is disposed in the direction in which the claw part 83A of the connector 5A' is flipped. As a result, the claw part side second surface 836 of the stepped part 832 of the claw part 83A of the connector 5A' collides against the engaging part side second surface 913 (see FIGS. 4(*c*) and 6). Due to such a collision, a locking sound is produced, which enables recognition of the locked condition. In addition, the locking sound is transmitted as a vibration to a hand of the operator (user), via the connectors 5A and 5A'. Such a locking sound and vibration enables the operator (user) to confirm the locked condition through both auditory and tactile sensations.

Moreover, as shown in FIG. 6, immediately upon colliding (immediately upon completion of the pressing operation), a gap 95 is generated between the claw part side first surface 835 of the claw part 83A of the connector 5A' and the engaging part side first surface 912 of the first female-side engaging part 91 of the connector 5A. This ensures that the collision is a comparatively strong collision, so that the locked condition can be recognized (confirmed) more assuredly.

The half-locked condition and the locked condition, as mentioned above, also are applied to the claw part 83A on the other side (the lower side in FIG. 4) of the connector 5A'.

As shown in FIG. 12, in the locked condition, the opening part 623 of the male connector section 6 of the connector 5A' presses in the axial direction against the top face 511 of the head part 50 of the connector 5A. As a result, the barrel part 55 becomes deformed (compressed) in the axial direction, and the head part 50 moves from the first cavity 731 into the second cavity 723. The head part 50, which has resided inside the first cavity 731 restricted by the inner peripheral surface 734 of the first cavity 731, now moves into the second cavity 723, such that the restriction on the outer peripheral surface of the head part 50 is released or moderated. Consequently, as a result of being compressed in the axial direction, the head part 50 can be enlarged sufficiently in diameter, in the directions of the arrows in FIG. 12, namely, the head part 50 can be deformed sufficiently. Therefore, the slit 512 can be opened assuredly and sufficiently. In addition, as a result, the liquid passage 621 in the male connector section 6 of the connector 5A', and the cavity (hollow portion) of the internal projection 725 of the female connector section 7B of the connector 5A, communicate with each other, i.e., are connected so as to permit liquid to flow therethrough via the valve element 51 (the slit 512). Accordingly, liquid can pass smoothly therethrough, for example, when an infusion, a transfusion, nutrient dosing, or the like, is carried out.

Further, in the locked condition, the opening part 623 of the male connector section 6 of the connector 5A' presses against the head part 50 of the valve element 51, in opposition to the urging force of the barrel part 55 of the valve element 51, so that the opening part 623 of the male connector section 6 and the top face 511 of the head part 50 (the valve element 51) are securely placed in contact with each other. Consequently, liquid-tightness at the connection between the male connector section 6 and the female connector section 7B can be maintained, i.e., such sections can securely be connected in a liquid-tight manner.

In addition, due to the urging force of the barrel part 55 of the valve element 51, the gap 95 between the claw part side first surface 835 of the claw part 83A of the connector 5A' and the engaging part side first surface 912 of the first female-side engaging part 91 of the connector 5A is eliminated, resulting in secure contact between the claw part side first surface 835 and the engaging part side first surface 912.

Release of the locked condition of the connector 5A' and the connector 5A (unlocking) is effected by operating the operating parts 93 of the connector 5A.

As shown in FIG. 7, the operating parts 93 are each pressed inwardly against the urging force of the urging part 84. This results in the claw part side first surface 835 of the claw part 83A (the stepped part 832) of the connector 5A' riding over the engaging part side first surface 912, while sliding on the engaging part side first surface 912 of the first female-side engaging part 91 of the connector 5A.

When the operating parts 93 are each pressed further, the claw part side first surface 835 of the claw part 83A of the connector 5A' vigorously (i.e., so as to flip) rides over the engaging part side first surface 912 of the first female-side engaging part 91 of the connector 5A (see FIG. 8). As a result, the locked condition is released. At the time of unlocking, an unlocking sound, which enables recognition of the unlocked condition, is generated. In addition, the unlocking sound is transmitted as a vibration to the operator's hand through the connectors 5A and 5A'. Such an unlocking sound and vibration enables the operator to confirm the unlocked condition through both auditory and tactile sensations.

This makes it possible for the operator to quickly carry out a subsequent operation, specifically, an operation of moving the connector 5A and the connector 5A' away from each other.

In addition, such an unlocked condition applies in the same manner to the claw part 83A on the other side (the lower side in FIG. 4) of the connector 5A'.

Further, in the unlocked condition, the slit 512 in the valve element 51 of the connector 5A becomes closed again, to assume the condition before connection of the connectors 5A, 5A'.

As has been described above, the locking sound is generated by the collision between the claw part side second surface 836 of the stepped part 832 of each of the claw parts 83A of the connector 5A' and the engaging part side second surface 913 of the first female-side engaging part 91 of the connector 5A (see FIG. 6). Also, the unlocking sound is generated by a process in which the claw part side first surface 835 of each of the claw parts 83A of the connector 5A' rides over the engaging part side first surface 912 of the first female-side engaging part 91 of the connector 5A (see FIG. 8).

Thus, sounds are generated at different locations, and therefore, the locking sound and the unlocking sound are different from each other in tone.

Since the locking sound and the unlocking sound are different from each other in tone and/or volume, it is possible, through hearing and perceiving the tone and/or volume of the sounds, to recognize whether the connectors are in the locked condition or in the unlocked condition.

In addition, since the two claw parts 83A are provided, and the two claw parts 83A are disengaged respectively from the first female-side engaging parts 91 at the time of unlocking, the unlocking sound (as well as the locking sound) is heard twice (two times), and the unlocked condition is not attained until this occurs. Incidentally, depending on the operation timing of the operating parts 93, specifically, in rare cases where disengagement of the claw parts 83A from the first female-side engaging parts 91 is effected substantially simultaneously, the unlocking sounds may be heard as if they were generated at a single point in time. However, in reality, such disengagement occurs twice (at two locations).

In the case that the unlocking sound is generated only once, only one of the two claw parts 83A becomes disengaged, while the other claw part 83A remains engaged. Therefore, the operator can judge that unlocking has not yet fully occurred.

The acute angle part 834 is preferably located so as to project from a plane (imaginary plane) 838 parallel to the direction of movement thereof (the plane contacts the line of intersection between the claw part side first surface 835 and the claw part side second surface 836) (see FIG. 8). This ensures that the tip (peak) of the acute angle part 834 rides over the projected part 911 of the first female-side engaging part instantaneously, so that a clear unlocking sound is likely to be generated. Similarly, a clear locking sound (locking connection sound) is likely to be generated.

In addition, the magnitude of the acute angle (angle θ (see FIG. 5)) of the acute angle part 834 is not particularly limited. For example, preferably, the angle is less than 90 degrees.

Where the angle θ resides within such a range of numerical values, the unlocking sound is generated more easily and reliably. Further, during both locking (the time of locking connection) and unlocking, deformation of the claw parts 83A is slight (restrained). This is advantageous in that the claw parts 83A are not susceptible to deformation, so that a clear locking sound and a clear unlocking sound are likely to be generated, even after the connectors have been used repeatedly.

As shown in FIG. 13, the infusion dosing section 2 has an indwelling needle or catheter (in this embodiment, an indwelling needle 21) to be left indwelling in a patient's blood vessel 110, and an infusion dosing section side connector 26, which is connected to a proximal portion of the indwelling needle or catheter (in this embodiment, the indwelling needle 21).

Concerning the material constituting the indwelling needle 21 (or catheter), depending on the indwelling site, a metallic needle such as a winged phleboclysis needle may be used. However, flexible polymeric materials, examples of which include thermoplastic resins, such as polyolefins, including polyethylene, polypropylene, etc., polyesters, and polyurethane, preferably are used.

The infusion dosing section side connector 26 includes a female lock section 9A and a female connector section 7A, which can be connected respectively with the male lock section 8A and the male connector section 6 of the connector 5A, which in turn is connected to the second infusion tube 4a, a similar female lock section 9B and a female connector section 7B, and a male connector section 263.

In addition, the axis of the male connector section 263 and the axis of the female connector section 7A substantially coincide with each other, whereas the axis of the female connector section 7B is substantially orthogonal to the axes thereof. In other words, the male connector section 263 and the female connector section 7A are oriented in opposite directions, whereas the female connector section 7B is oriented in a direction substantially orthogonal to the male connector section 263 and the female connector section 7A.

In the infusion dosing section side connector 26, a tube 24 that passes through a stop clamp 25 and which can be fixed in a stroke is connected to the male connector section 263 in a liquid-tight manner. A male connector section 23 is connected to the distal side of the tube 24. The male connector section 23 is not particularly limited, and may be any of a luer connector, a luer lock connector and the like, which can be connected to an outlet port 211 of the indwelling needle or catheter in a liquid-tight manner. Among these examples, a luer lock connector is preferred in particular.

The indwelling needle 21 includes the outlet port 211 disposed at a proximal portion thereof. The male connector section 23 attached to the infusion dosing section side connector 26 is connected to the outlet port 211 in a liquid-tight manner.

Next, the first infusion tube 4b and the second infusion tube 4a will be described below. Since the first infusion tube 4b and the second infusion tube 4a have the same configuration, the second infusion tube 4a will be described as representative.

The second infusion tube 4a has a tube 41 which is flexible (soft) and which constitutes an infusion passage, a connector 43 provided at an end portion on one side (distal portion) of the tube 41, and a piercing needle 451, which has a sharp needle tip, is provided on the other side (in this embodiment, at an end portion on the other side (proximal portion)) of the tube 41 and serves as a connecting part to be connected to the side of an infusion bag (infusion vessel) (containing section) 31 containing an infusion.

Examples of materials that can be used to constitute the tube 41 include flexible polyvinyl chloride, ethylene-vinyl acetate copolymer, polyethylene, polypropylene, and polybutadiene, as well as other materials containing such materials as principal constituents thereof.

In addition, slide type forceps (slide forceps) 46 and a drip cylinder 44 are provided respectively at intermediate positions of the tube 41, serving as a flow rate regulating means for regulating the flow rate of the infusion. The slide forceps 46 are not particularly limited, and conventionally known slide forceps can be used. Examples of forceps that are usable include the forceps described in Japanese Laid-Open Patent Publication No. 2004-49319, for example.

Further, the slide forceps 46 may be constituted by other types, such as a roller-type forceps, which can regulate the flow rate.

A predetermined infusion is contained in the infusion bag 31. When a stopper (rubber stopper) of the infusion bag 31 is penetrated (pierced) by the piercing needle 451, the infusion bag 31 and the second infusion tube 4a are connected to each other through the piercing needle 451, and as a result, the infusion can be supplied from the infusion bag 31 to the side of the second infusion tube 4a.

The drip cylinder 44 is disposed in the vicinity of the piercing needle 451. The drip cylinder 44 enables visual confirmation of the flow rate of the infusion.

In addition, a check valve 49 is disposed between the connector 43 and the drip cylinder 44. The check valve 49 is a one-way valve, permitting flow in only one direction, from the infusion bag 31 toward the connector 5A. The check valve 49 may be disposed at any location between the connector 43 and the drip cylinder 44. Preferably, however, the check valve 49 is disposed nearer to the connector 43, and more preferably, inside of the connector 43.

The check valve 49 has a valve main body formed with a pair of plate-like opening/closing members (not shown) inside thereof, wherein the opening/closing members are in firm contact with each other due to the elasticity (restoring forces) thereof, so that the passage in the check valve 49 is kept closed. In the case that the infusion flows in a direction from the distal side toward the proximal side, a pressure due to the infusion is exerted on outside surfaces of the opening/closing members, thereby placing the opening/closing members in firm contact with each other. Therefore, the infusion does not flow from the distal side toward the proximal side.

On the other hand, in the case that the infusion flow is directed from the proximal side toward the distal side, a predetermined pressure due to the infusion is exerted on the proximal side (tapered surface) of each of the opening/closing members, and the opening/closing members are displaced away from each other by the pressure, so that the passage in the check valve 49 opens. Consequently, the infusion flows from the proximal side toward the distal side.

While the check valve 49 may be omitted in some cases, e.g., where an assured injection is promised by an infusion pump or the like, it is preferable for the check valve 49 to be installed. According to the second infusion tube 4a, even if an infusion is administered by exerting a certain degree of pressure from the first infusion tube 4b connected to the connector 5A of the second infusion tube 4a, the check valve 49 prevents the infusion from flowing toward and into the upstream side (proximal side) of the second infusion tube 4a. Thus, the patient can be dosed with the infusion(s) in a reliable manner.

The connector 43 is disposed at a distal portion of the tube 41. The connector 43 has a male connector section 6 and a male lock section 8A. Such a configuration enables the connector 43 to be connected to the connector 5A.

Thus, the connector 5A, the connector 43 and the infusion dosing section side connector 26 are provided on at least one portion of the male lock section 8A and the female lock sections 9A and 9B. When such connectors are connected to one another, therefore, locking of them in twisted conditions can be prevented, as contrasted to the cases of screw type connectors, such as luer locks, according to the related art. In other words, by use of the aforementioned connection method, a condition in which the infusion tubes are aligned in a fixed direction can easily be maintained, even in cases where a large number of infusion tubes are interconnected.

Further, the connected condition of the male lock section 8A and the female lock section 9B can also assume the half-locked condition, as well as the locked condition.

For example, until the second infusion tube 4a is placed in use, the male connector section 6 of the connector 43 is loosely fitted in such a position so as not to open the valve element 51 disposed in the female connector section 7B of the connector 5A. Specifically, until the second infusion tube 4a is used, the connector 43 is connected to the connector 5A in a half-locked condition. This ensures that the valve element 51 is kept in a non-deformed condition until a point in time immediately before the valve element 51 permits the infusion to flow therethrough. Thus, the valve element 51 can be used without spoiling or diminishing the functionality thereof.

Further, in the locked condition, the male connector section 6 of the connector 43 and the female connector section 7B of the connector 5A are connected together in a liquid-tight manner, so that liquid can securely flow from the second infusion tube 4a into the connector 5A.

Now, operation (a method of use) of the infusion tube set 1 shall be described below.

A description will be made of a case where the second infusion tube 4a is used as a first infusion line (first infusion route) for dosing a patient with an infusion, and more specifically, as an infusion tube through which a basic liquid or the like principally flows, while the first infusion tube 4b is used as a second infusion line (second infusion route) for dosing the patient with an infusion, and more specifically, as an auxiliary route or an infusion tube through which, for example, a lipid emulsion, a therapeutic drug, an antibiotic agent or the like principally flows.

When the second infusion tube 4a is connected, first, for example, a maintenance medication is prepared in the infusion bag 31.

Next, the male connector section 6 of the connector 43 is pushed into the female connector section 7B of the connector 5A, so as to be fitted into the latter in a liquid-tight manner.

Subsequently, as shown in FIG. 13, a stopper (rubber stopper) of the infusion bag 31 containing the infusion is penetrated (pierced) by the piercing needle 451 of the second infusion tube 4a. Owing thereto, the infusion bag 31 and the second infusion tube 4a are connected to each other via the piercing needle 451, resulting in a condition in which the infusion can be supplied from the infusion bag 31 to the side of the second infusion tube 4a.

Next, the passage in the second infusion tube 4a is primed.

Subsequently, the male connector section 6 of the connector 5A of the second infusion tube 4a is inserted and fitted into the female connector section 7A of the infusion dosing section side connector 26, which is connected to the outlet port 211 of the indwelling needle 21 that has been set indwelling in a blood vessel 110 (e.g., a peripheral vein or the like) of a patient. As a result, the female connector section 7A of the infusion dosing section side connector 26 and the male connector section 6 of the connector 5A of the second infusion tube 4a are connected to each other in a liquid-tight manner. In this instance, the female lock section 9A of the infusion dosing section side connector 26 and the male lock section 8A of the connector 5A are placed in the locked condition, whereby easy disconnection thereof is prevented from occurring.

Next, by operating the slide forceps 46 of the second infusion tube 4a, the flow rate (dosing rate) of the infusion through the second infusion tube 4a is adjusted to a prescribed flow rate (prescribed dosing rate) for the maintenance medication, and dosing with the infusion is carried out in this condition.

Incidentally, the infusion dosing section side connector 26 may be omitted, such that the male connector section 6 of the connector 5A of the second infusion tube 4a is connected to the outlet port 211 of the indwelling needle 21.

Subsequently, when the first infusion tube 4b, which is used for administering, for example, an antibiotic agent at a predetermined time interval depending on the patient's condition, is connected, initially, physiological saline with the antibiotic agent dissolved therein is prepared in an infusion bag 32.

Next, the male connector section 6 of the connector 43 of the first infusion tube 4b is pushed into the female connector section 7B of the connector 5A, so as to be fitted to the latter in a liquid-tight manner.

Subsequently, a stopper (rubber stopper) of the infusion bag 32 containing the infusion is penetrated (pierced) by the piercing needle 451 of the first infusion tube 4b. Owing thereto, the infusion bag 32 and the first infusion tube 4b are connected to each other via the piercing needle 451, resulting in a condition in which the infusion can be supplied from the infusion bag 32 to the side of the first infusion tube 4b.

Next, the passage of the first infusion tube 4b is primed.

Subsequently, as shown in FIG. 14, the male connector section 6 of the connector 5A of the first infusion tube 4b is inserted into and fitted in the female connector section 7A of the connector 5A of the second infusion tube 4a. As a result, the female connector section 7A of the connector 5A of the second infusion tube 4a and the male connector section 6 of the connector 5A of the first infusion tube 4b are connected together in a liquid-tight manner. In this instance, the female lock section 9A of the second infusion tube 4a and the male lock section 8A of the first infusion tube 4b are placed in the locked condition, whereby easy disconnection thereof is prevented from occurring.

Next, by operating the slide forceps 46 of the first infusion tube 4b, the flow rate (dosing rate) of the infusion in the first infusion tube 4b is adjusted to a prescribed flow rate (prescribed dosing rate) for an antibiotic agent, and infusion is carried out in this condition.

In this manner, the patient can be dosed with the maintenance medication from the second infusion tube 4a and with the physiological saline containing the antibiotic agent dissolved therein from the first infusion tube 4b, respectively (can be dosed with a mixture of liquids).

Further, in the case that more infusion lines (infusion routes) are established, a male connector section 6 of a connector 5A of another infusion tube (not shown) is inserted and fitted into the female connector section 7A of the connector 5A of the first infusion tube 4b, in the same manner as mentioned above. Accordingly, the female connector section 7A of the connector 5A of the first infusion tube 4b and the male connector section 6 of the connector 5A of the other infusion tube are connected together in a liquid-tight manner.

Hereinafter, any number of infusion lines can be added in the same manner.

Incidentally, the method of using the infusion tube set 1 as mentioned above is merely one example thereof, and the method of use is not limited to the above-described example.

For example, in a case where the patient is dosed with an infusion from the second infusion tube 4a, the infusion may be supplemented by use of the first infusion tube 4b.

As described above, according to the infusion tube set 1, infusion tube connecting ports (the female connector sections 7A, 7B and the male connector section 6) are always provided, so that infusion lines (infusion routes) can be added easily, quickly and assuredly.

In other words, the infusion line connecting ports are always present, which eliminates a situation in which the number of infusion tube connecting ports might become insufficient, for example, upon an abrupt change in the patient's condition.

In addition, each of the infusion lines is liquid-tight.

Also, when an infusion line is added, it suffices simply to insert the male lock section 8A of the connector 5A on one side into the female lock section 9A or 9B of the connector 5A on the other side. Therefore, an infusion line can be added while dosing the patient with an infusion (for example, dosing the patient with a tiny quantity of a drug) through the infusion tube that is already connected. This makes it possible to avoid risks in which, for example, the concentration of the drug in the blood might be changed, leading to changes in symptoms.

In addition, at the time of adding an infusion line, it is unnecessary to open the infusion line(s) and to reconnect the infusion lines through reassembly thereof. This makes it possible to avoid a risk in which, for example, the number or frequency of chances for making an erroneous infusion line interconnection, or contamination of the route with bacteria, might be increased.

Incidentally, the number of the infusion tube(s) utilized in the infusion tube set according to the present invention may be one, or may be three or more.

Further, according to the present invention, if the infusion tube set includes a plurality of infusion tubes, the infusion tubes may be the same or may all be different from each other, or only a portion of the infusion tubes may be the same.

While the connector and the infusion tube set according to the present invention have been described with reference to the embodiment shown in the drawings, the present invention is not limited to this embodiment. The components of the connector and the infusion tube set may be replaced by other arbitrary configurations, which can exhibit functions the same or equivalent to those mentioned above. Additionally, arbitrary components or structures may be added to the aforementioned embodiment.

In addition, the number of female connector sections provided is not limited to two, and for example, three or more female connector sections may be provided.

Further, in the connectors, the male connector section and the male lock section correspond to each other, whereas the female connector section and the female lock section correspond to each other. However, correspondence between such sections is not limited in this manner. For example, a configuration may be adopted in which the male connector section and the female lock section correspond to each other, whereas the female connector section and the male lock section correspond to each other.

Industrial Applicability

The connector according to the present invention includes a male connector section having a cavity, a female connector section having a cavity to which another male connector section the same as the male connector section can be connected, a male lock section or a female lock section, disposed adjacent to the male connector section so that the connection direction thereof is parallel to that of the male connector section, a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled, and a seal member formed from an elastic material, for maintaining liquid-tightness of the connection between the other male connector section and the female connector section in a locked condition where the other male lock section and the female lock section are coupled to each other, wherein an unlocking sound, which enables recognition of unlocking, is generated at a time of unlocking when the locked condition is released. Therefore, unlocking, in which the unlocked condition is released, can be recognized (confirmed) by the sound (unlocking sound) thereof. In addition, the unlocking sound also is transmitted as a vibration to the operator's hand through the connector. Thus, by means of the connector, the unlocking sound enables the operator to confirm the unlocked condition through auditory and tactile sensations. Consequently, it is possible to securely avoid a situation in which, for example, the operator thinks that he or she has applied an unlocking operation to the connectors, which are in the locked condition, but wherein unlocking actually has not been achieved. Accordingly, the connector of the present invention has industrial applicability.

The invention claimed is:

1. A connector comprising:
a male connector section having a cavity;
a female connector section having a cavity to which another male connector section the same as the male connector section can be connected;
a male lock section or a female lock section, disposed adjacent to the male connector section so that the connection direction thereof is parallel to that of the male connector section;
a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and
a seal member formed from an elastic material, for maintaining liquid-tightness of the connection between the other male connector section and the female connector section in a locked condition where the other male lock section and the female lock section are coupled to each other, wherein:
the male lock section includes a pair of claw parts, which are capable of moving toward and away from each other, and an urging part provided on one end side of both the claw parts and operative to urge the claw parts so as to move the claw parts away from each other on the other end side;
the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other;
each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface; and
the engaging part has an engaging part side first surface, which makes contact with the claw part side first surface in the locked condition, and an engaging part side second surface, which makes contact with the claw part side second surface in the locked condition; and
wherein, by operating the operating part in the locked condition, the claw part side first surface of the stepped part is caused to ride over the engaging part side first surface, for generating an unlocking sound which enables recognition of unlocking.

2. The connector according to claim 1, wherein in the locked condition, the cavity of the other male connector section and the cavity of the female connector section communicate with each other so as to permit liquid to flow therethrough.

3. The connector according to claim 1, wherein the female lock section and the other male lock section are pressed in directions so as to move toward each other, at the time when the connector is placed in the locked condition.

4. The connector according to claim 3, wherein a gap is generated between the claw part side first surface and the engaging part side first surface, immediately upon completion of the pressing operation.

5. A connector comprising:
a male connector section having a cavity;
a female connector section having a cavity to which another male connector section the same as the male connector section can be connected;
a male lock section or a female lock section, disposed adjacent to the male connector section so that the connection direction thereof is parallel to that of the male connector section;
a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material, for maintaining liquid-tightness of the connection between the other male connector section and the female connector section in a locked condition where the other male lock section and the female lock section are coupled to each other, wherein:

the male lock section includes a pair of claw parts, which are capable of moving toward and away from each other, and an urging part provided on one end side of both the claw parts and operative to urge the claw parts so as to move the claw parts away from each other on the other end side;

the female lock section includes engaging parts capable of engagement respectively with the claw parts of the other male lock section, which are the same as those of the male lock section, and each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface;

wherein when an imaginary plane parallel to a direction of movement of the acute angle part is assumed, the acute angle part is located so as to project from the imaginary plane; and wherein an unlocking sound, which enables recognition of unlocking, is generated at a time of unlocking when the locked condition is released.

6. The connector according to claim 1, wherein a locking sound, which enables recognition of the locked condition, is generated when the connector is placed in the locked condition.

7. The connector according to claim 6, wherein the unlocking sound and the locking sound differ from each other in tone and/or in volume.

8. The connector according to claim 1, wherein the seal member is affixed to the cavity of the female connector section, and includes a surface that is placed in secure contact with an end part of the other male connector section in the locked condition, and a slit formed in the surface and which is opened in the locked condition.

9. The connector according to claim 1, comprising a plurality of the female connector sections, wherein at least one of the female connector sections and the male connector section are disposed such that center lines thereof are substantially orthogonal to each other.

10. The connector according to claim 1, comprising a plurality of the female connector sections, wherein at least one of the female connector sections and the male connector section are disposed such that center lines thereof are parallel to each other, and such that an opening part of the female connector section and an opening part of the male connector section are oriented in opposite directions.

11. A connector comprising:

a male connector section having a cavity;

a female connector section having a cavity to which another male connector section the same as the male connector section can be connected;

a male lock section or a female lock section, disposed adjacent to the male connector section so that the connection direction thereof is parallel to that of the male connector section;

a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material for maintaining liquid-tightness of the connection between the other male connector section and the female connector section in a locked condition where the other male lock section and the female lock section are coupled to each other, wherein the male lock section includes a pair of claw parts, which are capable of moving toward and away from each other, and an urging part provided on one end side of both the claw parts and operative to urge the claw parts so as to move the claw parts away from each other on the other end side, the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other, each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface, the engaging part has an engaging part side first surface, which makes contact with the claw part side first surface in the locked condition, and an engaging part side second surface, which makes contact with the claw part side second surface in the locked condition, wherein by operating the operating part in the locked condition, the claw part side first surface of the stepped part is caused to ride over the engaging part side first surface, for generating the unlocking sound, and the female lock section and the other male lock section are pressed in directions so as to move toward each other, at the time when the connector is placed in the locked condition, and a gap is generated between the claw part side first surface and the engaging part side first surface, immediately upon completion of the pressing operation.

12. A connector comprising:

a male connector section having a cavity;

a female connector section having a cavity to which another male connector section the same as the male connector section can be connected;

a male lock section or a female lock section, disposed adjacent to the male connector section so that the connection direction thereof is parallel to that of the male connector section;

a female lock section disposed adjacent to the female connector section so that the connection direction thereof is parallel to that of the female connector section, and to which another male lock section the same as the male lock section can be coupled, or a male lock section disposed adjacent to the female connector section so that the connection direction thereof is parallel to that of the female connector section, and to which another female lock section the same as the female lock section can be coupled; and a seal member formed from an elastic material for maintaining liquid-tightness of the connection between the other male connector section and the female connector section in a locked condition where the other male lock section and the female lock section are coupled to each other, wherein the male lock section includes a pair of claw parts, which are capable of moving toward and away from each other, and an urging part provided on one end side of both the claw parts and operative to urge the claw parts so as to move the claw parts away from each other on the other end side, the female lock section includes engaging parts capable of engagement respectively with the claw parts of the other male lock section, which are the same as those of the male lock section, and an operating part operable to cause both the claw parts of the other male lock section, which are the same as those of the male lock section, to move toward each other, each of the claw parts includes a stepped part provided at another end portion thereof, with a claw part side first surface being substantially parallel to the direction in which the claw parts move toward and away from each other, and with a claw part side second surface being substantially perpendicular to the claw part side first surface, and an acute angle part having a claw part side third surface, which is adjacent to the claw part side first surface and which forms an acute angle with the claw part side first surface, the engaging part has an engaging part side first surface, which makes contact with the claw part side first surface in the locked condition, and an engaging part side second surface, which makes contact with the claw part side second surface in the locked condition, wherein by operating the operating part in the locked condition, the claw part side first surface of the stepped part is caused to ride over the engaging part side first surface, for generating the unlocking sound; and when an imaginary plane parallel to a direction of movement of the acute angle part is assumed, the acute angle part is located so as to project from the imaginary plane.

13. An infusion tube set comprising:

the connector as set forth in claim 1; and a tube assembly having a tube, and a tube-side connector, which is disposed at one end portion of the tube, and which can be connected to the connector.

14. An infusion tube set comprising:

the connector as set forth in claim 11; and a tube assembly having a tube, and a tube-side connector, which is disposed at one end portion of the tube, and which can be connected to the connector.

15. An infusion tube set comprising:

the connector as set forth in claim 12; and a tube assembly having a tube, and a tube-side connector, which is disposed at one end portion of the tube, and which can be connected to the connector.

* * * * *